(12) United States Patent  (10) Patent No.: US 6,987,115 B2
Seefeld  (45) Date of Patent: Jan. 17, 2006

(54) ANTIBACTERIAL COMPOUNDS

(75) Inventor: Mark A. Seefeld, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/433,529

(22) PCT Filed: Dec. 7, 2001

(86) PCT No.: PCT/US01/48104

§ 371 (c)(1),
(2), (4) Date: Jun. 5, 2003

(87) PCT Pub. No.: WO02/062339

PCT Pub. Date: Aug. 15, 2002

(65) Prior Publication Data

US 2004/0053954 A1 Mar. 18, 2004

Related U.S. Application Data

(60) Provisional application No. 60/254,276, filed on Dec. 8, 2000.

(51) Int. Cl.
A61K 31/437 (2006.01)
C07D 471/04 (2006.01)
A61P 31/04 (2006.01)
(52) U.S. Cl. .......... 514/292; 546/85; 546/86; 546/87
(58) Field of Classification Search .......... 546/85, 546/86, 87; 514/292
See application file for complete search history.

(56) References Cited

U.S. PATENT DOCUMENTS 6,492,358 B2 * 12/2002 Sui et al. ............. 514/232.8

FOREIGN PATENT DOCUMENTS

WO  WO 00/72846  12/2000
WO  WO 01/87038  11/2001

OTHER PUBLICATIONS

Campos et al. Heterocycles (1980), 14(7), 975-84.*
Abdusalamov et al. Uzbekskii Khimicheskii Zhurnal (1964), 8(1), 48-50.*
Begum, et al., Arzneim-Forsch/Drug Res. , 1996, vol. 46, No. 11 pp. 1163-1168.
Arbain, et al., Aust. J. Chem., 1987, vol. 40, pp 1527-1536.
Database Beilstein—Institute for Organic Cemistry, 1928, vol. 99, pp. 668 XP002271425.
Database Beilstein—Institute for Organic Cemistry, 1955, vol. 88, pp. 1952-1954 XP002271426.
Database Beilstein—Institute for Organic Cemistry, 1970, vol. 6, pp. 1517 XP002271427.
Database Beilstein—Institute for Organic Cemistry, 1982, vol. 47, No. 25, pp. 4933-4936 XP002271428.
Database Beilstein—Institute for Organic Cemistry, 1988, vol. 53, No. 2, pp. 373-380 XP002271429.
Siddiqui, et al., Proc. Pakistan Acad. Sci., 1992, vol. 29, No. 4, pp. 285-298.
Siddiqui, et al., Proc. Pakistan Acad. Sci., 1990, vol. 27, No. 2, pp. 139-152.
Seefeld, et al., Bioorganic & Med. Chem. Letters, Oxford GB, 2001, pp. 2241-2244.

* cited by examiner

Primary Examiner—Evelyn Mei Huang
(74) Attorney, Agent, or Firm—Grace C. Hsu; Mary E. McCarthy; Charles M. Kinzig

(57) ABSTRACT

Compounds of the formula (I) are disclosed and are useful in the treatment bacterial infections:

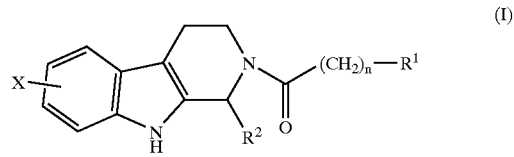

wherein:
$R^1$ is Ar or Het;
$R^2$ is $C_{1-6}$alkyl, $(R'')_2N-(CH_2)_m-$ or $Ar-C_{0-6}$alkyl;
X is H, $C_{1-4}$alkyl, OR', SR', $C_{1-4}$alkylsulfonyl, $C_{1-4}$alkylsulfoxyl, CN, $N(R')_2$, $CH_2N(R')_2$, $NO_2$, $CF_3$, $CO_2R'$, $CON(R')_2$, COR', NR'C(O)R', F, Cl, Br, I, or $CF_3S(O)_r-$;
R' is H, $C_{1-6}$alkyl or $Ar-C_{0-6}$alkyl;
each R'' independently is H, $C_{1-6}$alkyl or $Ar-C_{0-6}$alkyl;
m is 1 or 2;
n is 0, 1 or 2; and
r is 0, 1 or 2;
or a pharmaceutically acceptable salt thereof.

3 Claims, No Drawings

ANTIBACTERIAL COMPOUNDS

CROSS REFERENCES TO RELATED APPLICATIONS

This application is a National Stage Application filed under 35 U.S.C. §371 of PCT/US01/48104, filed Dec. 7, 2001, which claims priority to U.S. Provisional Application No. 60/254,276, filed Dec. 8, 2000.

FIELD OF THE INVENTION

This invention relates to pharmaceutically active compounds which are useful for the treatment of bacterial infections.

BACKGROUND OF THE INVENTION

The emergence of pathogens resistant to known antibiotic therapy is becoming a serious global healthcare problem (Chu, et al., (1996) *J. Med. Chem.*, 39: 3853–3874). Thus, there is a need to discover new broad spectrum antiobiotics useful in combating multidrug-resistant organisms.

Importantly, it has now been discovered that certain compounds have antibacterial activity, and, therefore, may be useful for (he treatment of bacterial infections in mammals, particularly in man.

SUMMARY OF THE INVENTION

This invention comprises compounds of the formula (I), as described hereinafter, which are useful in the treatment of bacterial infections.

This invention is also a pharmaceutical composition comprising a compound according to formula (I) and a pharmaceutically acceptable carrier. Additionally, this invention is a method of treating bacterial infections using compounds of formula (I).

DETAILED DESCRIPTION

This invention comprises compounds of formula (I):

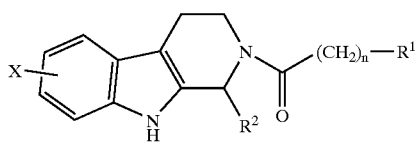

(I)

wherein:
R$^1$ is Ar or Het;
R$^2$ is C$_{1-6}$alkyl, (R")$_2$N—(CH$_2$)m— or Ar—C$_{0-6}$alkyl;
X is H, C$_{1-4}$alkyl, OR', SR', C$_{1-4}$alkylsulfonyl, C$_{1-4}$alkylsulfoxyl, CN, N(R')$_2$, CH$_2$N(R')$_2$, NO$_2$, CF$_3$, CO$_2$R', CON(R')$_2$, COR', NR'C(O)R', F, Cl, Br, I, or CF$_3$S(O)$_r$—;
R' is H, C$_{1-6}$alkyl or Ar—C$_{0-6}$alkyl;
each R" independently is H, C$_{1-6}$alkyl or Ar—C$_{0-6}$alkyl;
m is 1 or 2;
n is 0, 1 or 2; and
r is 0, 1 or 2;

or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as

and

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo.

The compounds of formula (I) are useful in the treatment of bacterial infections. Also, the compounds of this invention may be useful as antifungal agents. Additionally, the compounds may be useful in combination with known antibiotics.

With respect to formula (I):
Suitably, R$^1$ is phenyl, unsubstituted or substituted by methylenedioxy or by one to three substituents selected from the group consisting of C$_{1-4}$alkyl, OR', N(R')$_2$, F, Cl, Br, I, and CF$_3$.

Suitably, R$^2$ is (R")$_2$N—CH$_2$— or phenyl, unsubstituted or substituted by methylenedioxy or by one to three substituents selected from the group consisting of C$_{1-4}$alkyl, OR", CO$_2$R', N(R')$_2$, F, Cl, Br, I, and CF$_3$.

Suitably, X is H, C$_{1-4}$alkyl, OR', CN, N(R')$_2$, NO$_2$, CF$_3$, CO$_2$R', CON(R')$_2$, COR', F, Cl, Br or I.

Representative of the novel compounds of this invention are the compounds named in Examples 1–8 hereinafter.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

C$_{1-4}$alkyl as applied herein means an optionally substituted alkyl group of 1 to 4 carbon atoms, and includes methyl, ethyl, n-propyl, isopropyl, n-butyl, isobutyl and t-butyl. C$_{1-6}$alkyl additionally includes pentyl, n-pentyl, isopentyl, neopentyl and hexyl and the simple aliphatic isomers thereof. C$_{0-4}$alkyl and C$_{0-6}$alkyl additionally indicates that no alkyl group need be present (e.g., that a covalent bond is present).

Any $C_{1-4}$alkyl or $C_{1-6}$ alkyl may be optionally substituted with the group $R^x$, which may be on any carbon atom that results in a stable structure and is available by conventional synthetic techniques. Suitable groups for $R^x$ are $C_{1-4}$alkyl, OR', SR', $C_{1-4}$alkylsulfonyl, $C_{1-4}$alkylsulfoxyl, arylsulfonyl, arylsulfoxyl, $C_{1-4}$alkyl sulfonamides, aryl sulfonamides, —CN, N(R')$_2$, CH$_2$N(R')$_2$, —NO$_2$, —CF$_3$, —CO$_2$R'—CON(R')$_2$, —COR', —NR'C(O)R', F, Cl, Br, I, or CF$_3$S(O)$_r$—, wherein R' and r are as defined for formula (I) compounds.

Halogen or halo means F, Cl, Br, and I.

Ar, or aryl, as applied herein, means phenyl or naphthyl, or phenyl or naphthyl substituted by one to three substituents, such as those defined above for alkyl, or substituted by methylenedioxy.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazolyl, benzopyranyl, benzothienyl, furyl, imidazolyl, indolinyl, morpholinyl, piperidinyl, piperazinyl, pyrrolyl, pyrrolidinyle, tetrahydropyridinyl, pyridinyl, thiazolyl, thienyl, quinolinyl, isoquinolinyl, and tetra- and perhydro- quinolinyl and isoquinolinyl. Any accessible combination of up to three substituents on the Het ring, such as those defined above for alkyl, that are available by chemical synthesis and are stable are within the scope of this invention.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, EDC refers to 1-(3-dimethylaminopropyl)-3-ethylcarbodiimide, hydrochloride, HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

Generally, the compounds of formula (I) are prepared by reacting a compound of formula (II) with a compound of formula (III):

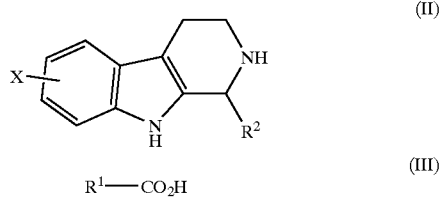

(II)

R$^1$—CO$_2$H (III)

wherein R$^1$, R$^2$ and X are as defined in formula (I), with any reactive functional groups protected, in the presence of EDC and HOBT;

and thereafter removing any protecting groups, and optionally forming a pharmaceutically acceptable salt.

In particular, compounds of formula (I) are prepared by the general methods described in Scheme I.

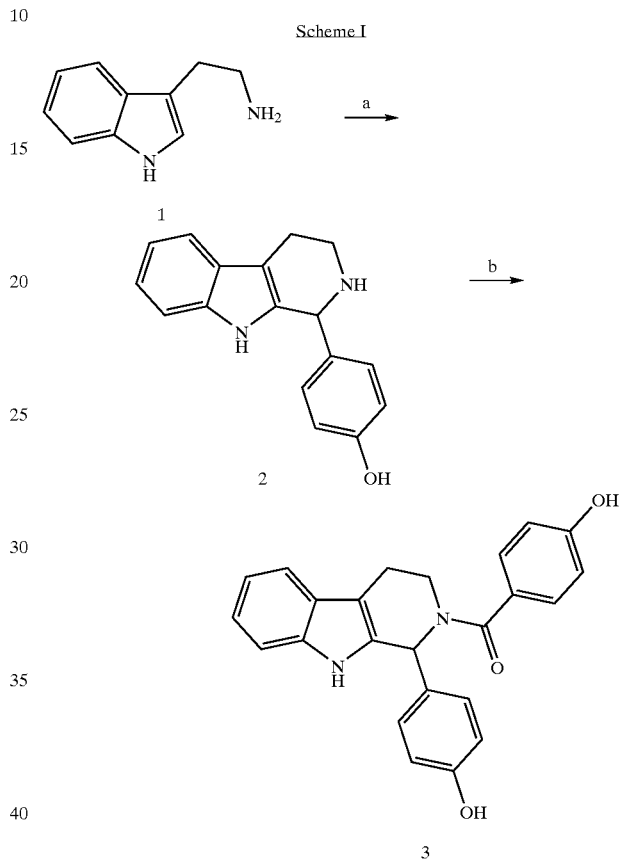

Scheme I

Reagents and conditions: (a) 4-hydroxybenzaldehyde, trifluoroacetic acid, dichloromethane; (b) 4-hydroxybenzoic acid, EDC, HOBt.H$_2$O, (i-Pr)$_2$NEt, DMF.

Commercially available tryptamine (I-1) is treated with an anhydrous acid such trifluoroacetic acid, in the presence of an aldehyde or an acid labile aldehyde equivalent, for example an acetal, to afford I-2. The use of protecting groups to mask reactive functionality is well-known to those of skill in the art, and other protecting groups are listed in standard reference volumes, such as Greene, "Protective Groups in Organic Synthesis" (published by Wiley-Interscience). The amine derivative I-2 is then converted to amide I-3 by reaction with an activated derivative of a suitable carboxylic acid. For example, 4-hydroxybenzoic acid is converted to an activated form by reaction with EDC and HOBt, and the activated form is subsequently reacted with amine I-2 in a suitable solvent such as DMF, CH$_2$Cl$_2$, or CH$_3$CN. Depending on whether acid neutralization is required, an added base, such as triethylamine (Et$_3$N), diisopropylethylamine ((i-Pr)$_2$NEt), or pyridine, may be used. Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag).

Amide coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Typically, the amine is coupled via its free amino group to an appropriate carboxylic acid substrate using a suitable carbodiimide coupling agent, such as N,N'dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine, optionally in the presence of a base, are also suitable. For example, a benzoic acid is treated in an anhydrous solvent, such as methylene chloride or tetrahydrofuran (THF), in the presence of a base, such as N-methylmorpholine, DMAP or a trialkylamine, with isobutyl chloroformate to form the "activated anhydride", which is subsequently reacted with the free amine.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example, animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Also, the compounds of this invention may be useful as antifungal agents. Additionally, the compounds may be useful in combination with known antibiotics.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compound was tested in serial two-fold dilutions ranging from 0.06 to 64 mcg/mL. Test organisms were selected from the following laboratory strains: *Staphiylococcits aureus* Oxford, *Staphylococcus aureus* WCUH29, *Streptococcus pneumoniae* ERY2, *Streptococcus pneumoniae* 1629, *Streptococcus pneumoniae* N 1387, *Enterococcus faecalis* I, *Enterococcus faecalis* 7, *Haeinophilus infliuenzae* Q1, *Haemophilus influenzae* NEMC1, *Moraxella Catarrhalis* 1502, *Escherichia coli* 7623 AcrABEFD+, *Escherichia coli* 120 AcrAB-, *Escherichia coli* MG1655, *Escherichia coli* MG1658. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 $\mu$g/mL to be a potential lead compound. Preferably, the compounds used in the antimicrobial assays of the present invention have a MIC value of less than 128 $\mu$g/mL. Most preferably, said compounds have a MIC value of less than 64 $\mu$g/mL.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at 300 MHz, and chemical shifts are reported in parts per million ($\delta$) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 4-(1,2,3,4-tetrahydrobeta-carbolinyl)phenol

To a stirred solution of tryptamine (5.0 g, 31.2 mmole) in dry CH$_2$Cl$_2$ (100 mL) at RT was added 4-hydroxybenzaldehyde (3.81 g, 31.2 mmole) followed by dropwise addition of trifluoroacetic acid (7.11 g, 62.4 mmole). After 12 hr, the reaction solution was washed with 10% aqueous NaHCO$_3$ (100 mL), H$_2$O (100 mL) and brine. The organic solution was dried over Na$_2$SO$_4$ and concentrated under reduced pressure to give a yellow oil. The yellow residue was washed with hexanes and dried under high vacuum to afford the title compound (7.74 g, 94%) as a light yellow solid: MS (ES) m/e 265 (M+H)$^+$.

Preparation 2

Preparation of methyl 4-(1,2,3,4-tetrahydrobeta-carbolinyl)benzoate

According to the procedure of Preparation 1, except substituting 4-carboxymethyl benzaldehyde (0.82 g, 5.0 mmole) for 4-hydroxybenzaldehyde, the title compound (1.45 g, 95%) was prepared as a light yellow solid: MS (ES) m/e 307 (M+H)$^+$.

Preparation 3

Preparation of 1-(4-fluorophenyl)-1,2,3,4-tetrahydrobeta-carboline

According to the procedure of Preparation 1, except substituting 4-fluorobenzaldehyde (0.62 g, 5.0 mmole) for 4-hydroxybenzaldehyde, the title compound (1.29 g, 97%) was prepared as a light yellow solid: MS (ES) m/e 267 (M+H)$^+$.

Preparation 4

Preparation of [(6-methyl(1,2,3,4-tetrahydrobeta-carbolinyl)methyl]dimethylamine dihydrochloride To a stirred suspension of 6-methyltryptamine hydrochloride (2.00 g, 9.5 mmole) and dimethylaminoacetaldehyde diethyl acetal (1.53 g, 9.5 mmole) in dry n-butanol (45 mL) at RT was added concentrated hydrochloric acid (1.6 mL, 19.0 mmole). The reaction solution was heated to reflux under an atmosphere of nitrogen. After 6 hr, the reaction solution was cooled to RT without stirring for 12 hr. The precipitate was filtered and then washed sequentially with n-butanol and diethyl ether. Drying under high vacuum afforded the title compound (0.74 g, 25%) as a light yellow solid: MS (ES) m/e 244 (M+H-2HCl)$^+$.

Preparation 5

Preparation of [(6-chloro(1,2,3,4-tetrahydrobeta-carbolinyl)methyl]dimethylamine dihydrochloride According to the procedure of Preparation 4, except substituting 6-chlorotryptamine hydrochloride (2.30 g, 10.0 mmole) for 6-methyltryptamine hydrochloride, the title compound (1.00 g, 30%) was prepared as a light yellow solid: MS (ES) m/e 337 (M+H)$^+$.

Preparation 6

Preparation of [(1,2,3,4-tetrahydrobeta-carbolinyl)methyl]dimethylamine dihydrochloride According to the procedure of Preparation 4, except substituting tryptamine hydrochloride (1.96 g, 10.0 mmole) for 6-methyltryptamine hydrochloride, the title compound (0.85 g, 28%) was prepared as a light yellow solid: MS (ES) m/e 303 (M+H)$^+$.

The following examples illustrate methods for preparing the biologically active compounds of this invention from intermediate compounds such as those described in the foregoing Preparations.

Example 1

Preparation 2-(2,4-dichlorophenyl)-1-{1-[(dimethylamino)methyl](1,2,3,4-tetrahydrobeta-carbolin-2-yl)}ethan-1-one To a stirred solution of [(1,2,3,4-tetrahydrobeta-carbolinyl)methyl]dimethylamine dihydrochloride (0.85 g, 2.80 mmole) in dry DMF (20 mL) at RT was 2,4-dichlorophenylacetic acid (0.63 g, 3.08 mmole), 1-hydroxybenzotriazole hydrate (0.42 g, 3.08 mmole) and diisopropylethylamine (1.19 g, 9.24 mmole). After 10 min, EDC (0.59 g, 3.08 mmole) was added and the reaction was allowed to stir for 12 hr. The reaction contents were poured into $H_2O$ (100 mL) and extracted with EtOAc (2×100 mL). The combined organic phases were washed sequentially with $H_2O$ and brine. Drying the organic phase over $Na_2SO_4$ and concentration under reduced pressure gave a yellow oil. Purification on silica [(CHCl$_3$/CH$_3$OH, 95:5 (containing 5% NH$_4$OH)] afforded the title compound (1.05 g, 90%) as a yellow solid: MS (ES) m/e 417 (M+H)$^+$.

Example 2

Preparation 3,4-dichlorophenyl-1-[(dimethylamino)methyl]-6-chloro-(1,2,3,4-tetrahydrobeta-carbolin-2-yl)}ethan-1-one According to the procedure of Example 1, except substituting [6-chloro(1,2,3,4-tetrahydrobeta-carbolinyl)methyl]dimethylamine dihydrochloride (1.00 g, 2.98 mmole) for [(1,2,3,4-tetrahydrobeta-carbolinyl)methyl]dimethylamine dihydrochloride and substituting 3,4-dichloroacetic acid (0.42 g, 3.27 mmole) for 2,4-dichlorophenylacetic acid, the title compound (1.30 g, 89%) was prepared as a light yellow solid: MS (ES) m/e 437 (M+H)$^+$.

Example 3

Preparation 3,4-dichlorophenyl-1-[(dimethylamino)methyl]-6-methyl-( 1,2,3,4-tetrahydrobeta-carbolin-2-yl)}ketone According to the procedure of Example 1, except substituting [6-methyl(1,2,3,4-tetrahydrobeta-carbolinyl)methyl]dimethylamine dihydrochloride (0.85 g, 2.81 mmole) for [(1,2,3,4-tetrahydrobeta-carbolinyl)methyl]dimethylamine dihydrochloride and substituting 3,4-dichloroacetic acid (0.40 g, 3.10 mmole) for 2,4-dichlorophenylacetic acid, the title compound (1.05 g, 90%) was prepared as a light yellow solid: MS (ES) m/e 417 (M+H)$^+$.

Example 4

Preparation 1-(4-fluorophenyl)(1,2,3,4-tetrahydro-beta-carbolin-2-yl)-4-hydroxyphenyl ketone To a stirred solution of 1-(4-fluorophenyl)-1,2,3,4-tetrahydrobeta-carboline (0.70 g, 2.63 mmole) in dry DMF (20 mL) at RT was added 4-hydroxybenzoic acid (0.40 g, 2.89 mmole), 1-hydroxybenzotriazole hydrate (0.39 g, 2.89 mmole) and diisopropylethylamine (0.36 g, 2.89 mmole). After 10 min, EDC (0.55 g, 2.89 mmole) was added and the reaction was allowed to stir for 12 hr. The reaction contents were poured into $H_2O$ (100 mL) and extracted with EtOAc (2×100 mL). The combined organic phases were washed sequentially with $H_2O$ and brine, then were dried over $Na_2SO_4$. Concentration under reduced pressure gave a yellow solid. Purification on silica (hexanes/EtOAc, 1:2) afforded the title compound (0.94 g, 93%) as a light yellow solid: MS (ES) m/e 387 (M+H)$^+$.

Example 5

Preparation 1-(3-chloro-4-fluorophenyl)(1,2,3,4-tetrahydrobeta-carbolin-2-yl)-4-hydroxyphenyl ketone According to the procedure of Example 4, except substituting 3-chloro-4-hydroxybenzoic acid hemihydrate (0.39 g, 2.15 mmole) for 4-hydroxybenzoic acid, the title compound (0.78 g, 95%) was prepared as a light yellow solid: MS (ES) m/e 420 (M+H)$^+$.

Example 6

Preparation methyl 4-{2-[(hydroxyphenyl)carbonyl]-1,2,3,4-tetrahydrobeta-carbolinyl}benzoate According to the procedure of Example 4, except substituting methyl 4-(1,2,3,4-tetrahydrobeta-carbolinyl)benzoate (0.50 g, 1.63 mmole) for 1-(4-fluorophenyl)-1,2,3,4-tetrahydrobeta-carboline, the title compound (0.65 g, 94%) was prepared as a light yellow solid: MS (ES) m/e 427 (M+H)$^+$.

Example 7

Preparation 4-hydroxy-3-methylphenyl 1-(4-hydroxyphenyl)(1,2,3,4-tetrahydrobeta-carbolin-2-yl) ketone)

According to the procedure of Example 4, except substituting 4-(1,2,3,4-tetrahydrobeta-carbolinyl)phenol (0.50 g, 1.89 mmole) for 1-(4-fluorophenyl)-1,2,3,4-tetrahydrobetacarboline and substituting 4-hydroxy-3-methylbenzoic acid (0.32 g, 2.08 mmole) for 4-hydroxybenzoic acid, the title compound (0.70 g, 93%) was prepared as a light yellow solid: MS (ES) m/e 399 (M+H)$^+$.

Example 8

Preparation 4-hydroxyphenyl 1-(4-hydroxyphenyl)(1,2,3,4-tetrahydrobeta-carbolin-2-yl) ketone According to the procedure of Example 4, except substituting 4-(1,2,3,4-tetrahydrobeta-carbolinyl)phenol (0.50 g, 1.89 mmole) for 1-(4-fluorophenyl)-1,2,3,4-tetrahydrobetacarboline, the title compound (0.66 g, 91%) was prepared as a light yellow solid: MS (ES) m/e 385 (M+H)$^+$.

Example 9

Parenteral Dosage Unit Composition

A preparation which contains 20 mg of the compound, of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 10

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 11

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound which is:
   2-(2,4-dichlorophenyl)-1-{1-[(dimethylamino)methyl](1,2,3,4-tetrahydrobeta-carbolin-2-yl)}ethan-1-one;
   3,4-dichlorophenyl 1-[(dimethylamino)methyl]-6-chloro (1,2,3,4-tetrahydrobeta-carbolin-2-yl) ketone;
   3,4-dichlorophenyl 1-[(dimethylamino)methyl]-6-methyl (1,2,3,4-tetrahydrobeta-carbolin-2-yl) ketone;
   1-(4-fluorophenyl)(1,2,3,4-tetrahydrobeta-carbolin-2-yl)-4-hydroxyphenyl ketone;
   1-(3-chloro-4-fluorophenyl)(1,2,3,4-tetrahydrobeta-carbolin-2-yl)-4-hydroxyphenyl ketone;
   methyl 4-{2-[(4-hydroxyphenyl)carbonyl]-1,2,3,4-tetrahydrobeta-carbolin-2-yl}benzoate;
   4-hydroxy-3-methylphenyl 1-(4-hydroxyphenyl)(1,2,3,4-tetrahydrobeta-carbolin-2-yl) ketone; or
   4-hydroxyphenyl 1-(4-hydroxyphenyl)(1,2,3,4-tetrahydrobeta-carbolin-2-yl) ketone;
   or a pharmaceutically acceptable salt thereof.

2. A pharmaceutical composition which comprises a compound according to any one of claims 1 and a pharmaceutically acceptable carrier.

3. A method of treating bacterial infections which comprises administering to a subject in need thereof an antibacterially effective amount of a compound according to claim 1.

* * * * *